United States Patent [19]
Gundolf

[11] Patent Number: 5,571,105
[45] Date of Patent: Nov. 5, 1996

[54] OSTEOSYNTHESIS APPARATUS FOR THE FIXATION OF BONE FRAGMENTS

[76] Inventor: Ferdinand Gundolf, Kemterstr. 1/I, A-6330 Kufstein, Austria

[21] Appl. No.: 271,048

[22] Filed: Jul. 6, 1994

[30] Foreign Application Priority Data

Jul. 6, 1993 [DE] Germany .......................... 43 22 507.1

[51] Int. Cl.⁶ .............................. A61B 17/82; A61B 17/68
[52] U.S. Cl. ..................................... 606/74; 606/72; 24/21
[58] Field of Search ................................ 606/74, 72, 60, 606/54, 53, 103, 140, 205, 207; 403/291, 393; 24/20 R, 21, 22, 23 R, 23 B

[56] References Cited

U.S. PATENT DOCUMENTS

| 281,821 | 7/1883 | Arnold | 24/21 |
| 2,291,413 | 7/1942 | Siebrandt | 606/103 |
| 4,223,673 | 9/1980 | Harris | 606/205 |
| 5,366,461 | 11/1994 | Blasnik | 606/74 |

FOREIGN PATENT DOCUMENTS 4200757 7/1992 Germany.

Primary Examiner—Stephen C. Pellegrino
Assistant Examiner—Scott B. Markow
Attorney, Agent, or Firm—Andrus, Sceales, Starke & Sawall

[57] ABSTRACT

Apparatus for the osteosynthesis of bone fragments, in particular for the fixation of bone fractures comprises a retaining strap that wraps around the fracture or the bone in the region of the site to be treated. The retaining strap is in the form of a flat strip typically in the nature of a hose- or pipe-clamp. At one end of the retaining strap, which is intended to be that end which contacts the bone, there is provided a receiving element through which the other end of the retaining strap can be passed and fixed in position to hold the strap in place under tension when wrapped around the bone. The receiving element is mounted so that it can be rotated about an axis substantially perpendicular to the flat surface of the retaining strap.

14 Claims, 3 Drawing Sheets

OSTEOSYNTHESIS APPARATUS FOR THE FIXATION OF BONE FRAGMENTS

FIELD OF THE INVENTION

The present invention relates to an apparatus for the osteosynthesis of bone fragments, in particular for the fixation of bone fractures, and to surgical instruments for use therewith.

DESCRIPTION OF THE PRIOR ART

The primary aim in the treatment of fractures is to restore the function of the injured limb. To avoid misalignments and to prevent fracture diseases, such as stiffened joints and damage to the soft parts as a result of circulatory disorders, it is desirable to stabilize the broken bone by firm osteosynthesis to such an extent that prolonged external fixation by plaster casts or the like is unnecessary and active movement therapy of the injured limb can be begun immediately. Similarly, in reconstructive surgery on the skeleton emphasis is placed on an early active functional treatment as well as on reliable ossification. Additional important considerations are a shorter stay in the hospital, the soonest possible restoration of the load-bearing capacity of the bone and, in particular, a reduction of the time needed for the operation. These aims have been substantially achieved by the apparatus described in German Patent DE 42 00 757 A1, which was originated by the inventor of the present invention, and has been successfully employed in practice. However, experience has shown that more favorable results would be obtained if the retaining strap were more flexible. This would achieve a better fit between the retaining strap and the surface of the bone, so that the entire surface of the retaining strap would be in contact with the bone over the full length of the encircling section.

SUMMARY OF THE INVENTION

According to a first aspect of the present invention there is provided apparatus for the osteosynthesis of bone fragments comprising a retaining strap in the form of a flat strip that can be wrapped around a bone in the region of a site to be treated, a receiving element provided at one end of the strap through which the other end of the retaining strap can be passed and fixed in position to hold the strap in place under tension when wrapped around the bone, and wherein the improvement comprises the receiving element being mounted to the strap so that it can be rotated about an axis substantially perpendicular to the flat surface of the retaining strap.

Because the receiving element is rotatable about an axis approximately perpendicular to the flat surface of the retaining strap, the retaining strap can be made to fit more closely to conically shaped sections of bone, in such a way that all along the section wrapped around the bone, practically the full surface area of the strap is in contact with the bone. The retaining strap thus wraps like a collar around the bone or the bone fracture to be fixed. This arrangement largely avoids a linear or tangential contact between retaining strap and bone and has a correspondingly gentle and tolerable action on the bone.

Preferably, at least one spike that can penetrate bone is provided at said one the end of the retaining strap on the surface of the end intended to face the bone.

The spike prevents the retaining strap from slipping when it is wrapped around the bone and tightened. Additional spikes or thorns can be provided for this purpose on the surface of the retaining strap that faces the bone, but preferably only on that half of the strap to which the receiving element is attached.

Preferably also, the receiving element comprises a flat strip bent into a sleeve defining a substantially rectangular bore with a cross-sectional area corresponding to the cross-sectional area of the retaining strap so that said other end of the strap can be passed through the sleeve with clearance.

Preferably also, the receiving element is mounted to the strap by a swivel pin which protrudes from the surface of the retaining strap intended to face the bone in the shape of a spike. Thus, swivel pin of the receiving element has a dual function.

Preferably also, radial serrations in a star pattern centered on said axis are provided on the side of the rotatably mounted receiving element that faces the retaining strap and/or on the surface of said retaining strap that faces the receiving element. This increases the rotational stability between the receiving element and the associated end section of the retaining strap after the latter has been tightened and fixed.

Alternatively, the receiving element defines a funnel-shaped aperture opening towards said one end of the retaining strap and/or an opposite direction thereto. In this embodiment a swivel mounting of the receiving element on the associated end section of the retaining strap is in some circumstances unnecessary. However, this embodiment can also be combined with the first-mentioned, so that the retaining strap can be fitted more closely to the surface of the bone. Preferably the receiving element is also formed as a flat sleeve in this embodiment.

Preferably also, the receiving element can be tilted in all directions relative to its mounting to the strap within predefined limits such as in the range of 5° to 25° inclusive. This can be achieved by mounting the receiving element to the strap by a swivel pin which is of flexible construction or by mounting the receiving element to the strap by a swivel pin with sufficient clearance to permit the element to be tilted in all directions within the predefined limits. Such an arrangement further increases the flexibility of the retaining strap.

Preferably also, a bone spike is provided that can be moved along the retaining strap. In one embodiment the movable bone spike is disposed on the bone-facing surface of a sleeve which can slide along the strap and which preferably comprises a substantially U-shaped slide. This is particularly useful for fixing loose bone fragments and also prevents undesired slippage of the retaining strap when it is wrapped around the bone and tightened.

According to a second aspect of the present invention there is provided forceps for use with an apparatus according to the first aspect of the present invention and comprising jaws of which one jaw is substantially semicircular in shape whereby a free end thereof can be passed around a bone and positioned on a back side thereof opposite an access site, and a holding means disposed at said free end capable of moving said bone spike along the retaining strap when wrapped around the bone.

According to a third aspect of the present invention there is provided apparatus for producing a bore for a bone spike comprising a shaft, a cross bar at one end of the shaft, and a pointed conical drill-bit at the other end of the shaft.

Further features, advantages and details of the invention will become apparent from the following description of some preferred embodiments of the invention with reference to the accompanying drawings.

DESCRIPTION OF THE PREFERRED EMBODIMENTS

Figure 5:
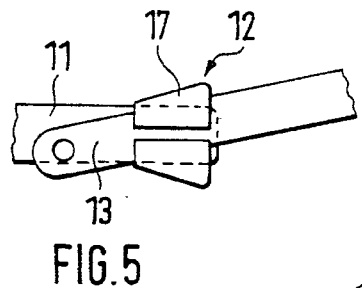
FIG. 5 is a plan view of an alternative embodiment of a receiving element.

Apparatus for the osteosynthesis of bone fragments, in particular for the fixation of bone fractures, according to the present invention and as shown in FIGS. 1 to 4 comprises a retaining means that is wrapped around the fracture or the bone in the region of the site to be treated. The retaining means takes the form of a flat, ribbon-like retaining strap 10. At one end of the strap 10, namely an end section 11 which is positioned next to the bone, a receiving element 12 is disposed through which can be passed the other end of the retaining strap 10, namely an end section 13 which is positioned spaced from the bone. After the retaining strap 10 has been tightened around the bone, the part of the end section 13 that has been passed through the receiving element 12 is bent up and back, so that the end sections 11 and 13 will remain in the positions to which they have been adjusted relative to one another. In this way the end section 13 of the retaining strap 10 is fixed to the receiving element 12, as hereinafter described.

Figure 3:
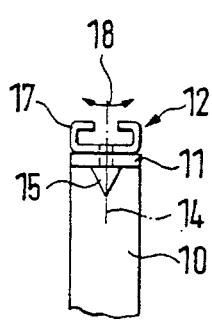
FIG. 3 is an end view of the receiving element in the direction of Arrow III in FIG. 1.
Figure 2:
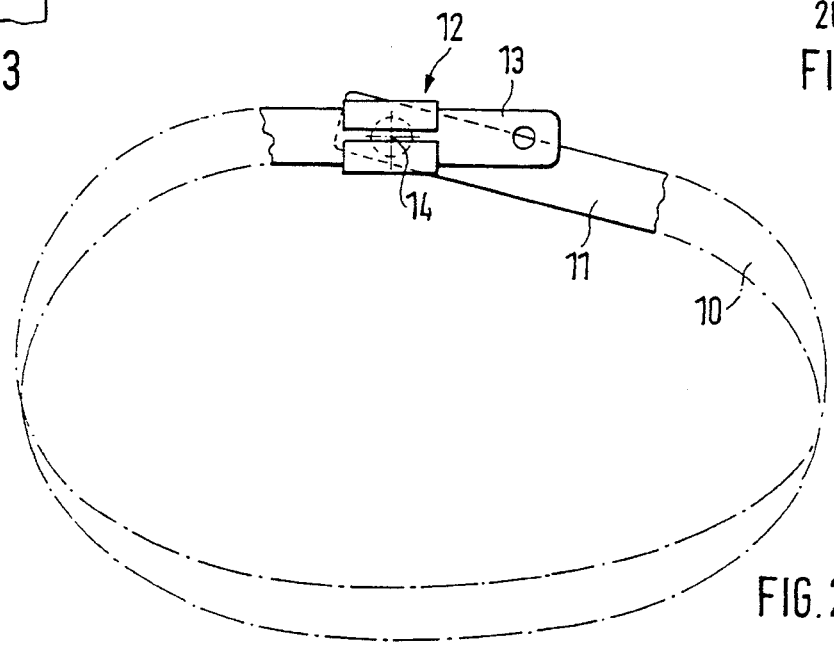
FIG. 2 is a view similar to FIG. 1 showing a receiving element forming part of the strap when in a swivelled position.
Figure 2A:
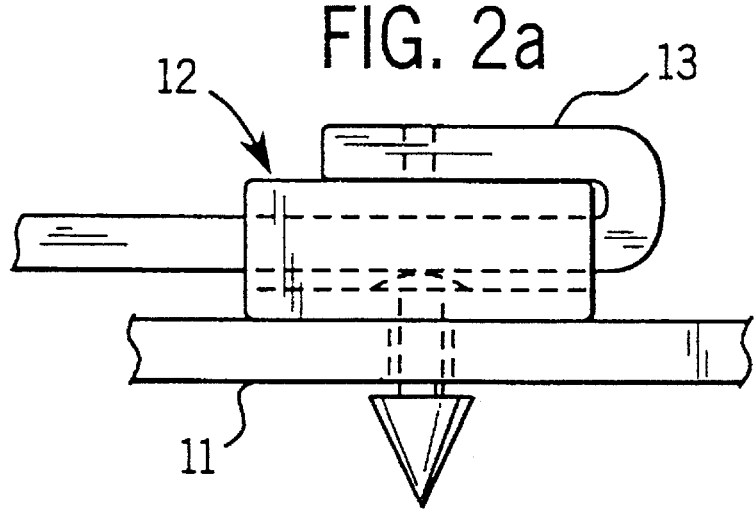
FIG. 2a is a fragmentary side view illustrating the releasable connection of the strap as applied to a bone structure as originally shown.

As shown in FIGS. 2 and 3, the receiving element 12 is so disposed that it can rotate about an axis perpendicular to the flat surface of the retaining strap 10 by means of a swivel pin 14 (see especially FIG. 2). This arrangement enables the retaining strap to be fitted more closely to the surface of a bone, in particular to an approximately conically shaped bone surface. As most clearly shown in FIGS. 2 and 2a, the outer end section 13 of the strap 10 is bent backwardly over the sleeve 12 after the restraining strap has been tightened around the bone, as previously described. This establishes a fixed interconnection of the strap to itself and defines a releasable connector as a result of the interconnection consisting of the sleeve as a first member connected to the strap and a second member formed as a part of or connected to the second end 13.

In order to fix the end section 11 of the retaining strap 10, on the surface of the end section 11 that faces the bone there is disposed at least one spike or thorn 15 that can penetrate the bone. As shown in FIG. 3, the swivel pin 14 of the receiving element 12 protrudes beyond the bone-facing surface of the end section 11 of the retaining strap 10 associated with the receiving element 12, and this protruding portion has the shape of a spike or thorn 15. The swivel pin 14 thereby has a dual function. It serves simultaneously as an axle about which the receiving element 12 can rotate and as a means of fixing the end section 11 of the retaining strap 10 to the bone. The retaining strap 10 is thus prevented from slipping while it is being wrapped around the bone and tightened.

Figure 1:
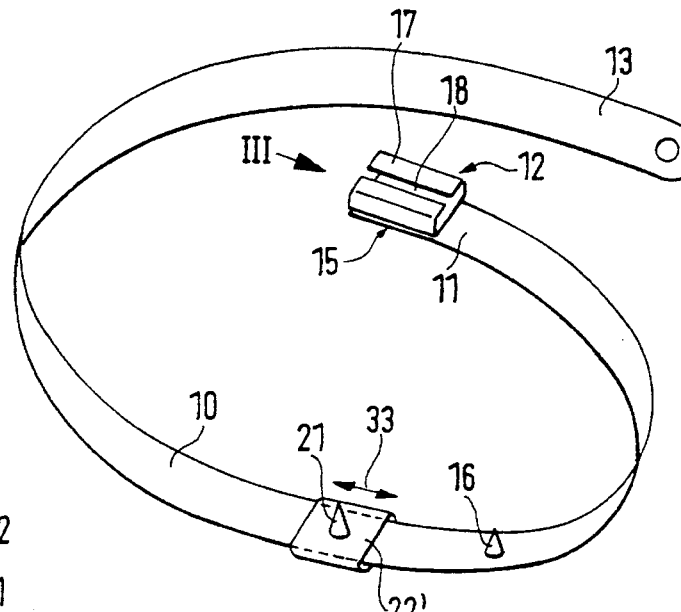
FIG. 1 is a perspective view of a retaining-strap apparatus in accordance with the present invention.

As shown in FIG. 1, on the surface of the retaining strap 10 that faces the bone an additional spike or thorn 16 is disposed. It is situated in the half of the retaining strap 10 closest to the receiving element 12.

The receiving element 12 in this illustrated embodiment is formed by a piece of retaining strap bent into a flat sleeve 17, the open, approximately rectangular cross-sectional area of which corresponds to the cross section of the retaining strap 10 in such a way that the other end 13 of the retaining strap spaced from the bone can be passed through the flat sleeve 17 with clearance. This embodiment is particularly simple to manufacture. In particular, in this embodiment the swivel pin 14 can be simply fixed in position. The flat sleeve 17 is divided by a longitudinal slot 18 on its upper surface and to fix the swivel pin 14, the two upper halves of the flat sleeve 17 are bent outward slightly. After the swivel pin 14 has been fixed, these two halves are bent back again, so that the flat sleeve has the shape shown in FIGS. 1, 2 and 3. The swivel pin 14 itself is formed by a rivet, in which the head toward the bone is shaped as a pointed cone to form the spike or thorn 15 mentioned above. The rotatability of the receiving element 12 or the flat sleeve 17 relative to the end section 11 of the retaining strap 10 is indicated in FIG. 3 by the double arrow 18. In this regard see also FIG. 2.

Figure 4:
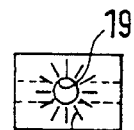
FIG. 4 is a view from below of the receiving element.

As shown in FIG. 4, on the surface of the rotatably mounted receiving element 12 that faces the retaining strap 10 or the end section 11 thereof radial serrations 20 are disposed in a star pattern centered on the swivel pin 14 or a bore 19 that receives the swivel pin 14. In the same way, complementary radial serrations can also be provided on the surface of the retaining strap or its end section 11 that faces the receiving element 12. By this means, after fixation of the retaining strap rotational stability between the receiving element 12 and the associated end section 11 of the retaining strap 10 is ensured.

The retaining strap and the receiving element 12 are preferably made of a titanium alloy compatible with human tissue.

FIG. 5 shows an alternative embodiment in which the receiving element 12 again has the form of a flat sleeve 17 but is funnel-shaped, with a wider opening toward the free end of the associated retaining-strap end section 11. In this embodiment it is not absolutely necessary for the receiving element 12 to be rotatably disposed as in the embodiment previously described with reference to FIGS. 1 to 3. If it is thus disposed, however, the retaining strap will have greater flexibility and can be more closely fitted to various surface configurations of bones to be treated. The flat sleeve 17 can also be funnel-shaped in the opposite direction. A double funnel, with widened openings at both ends, is also conceivable.

Figure 4A:
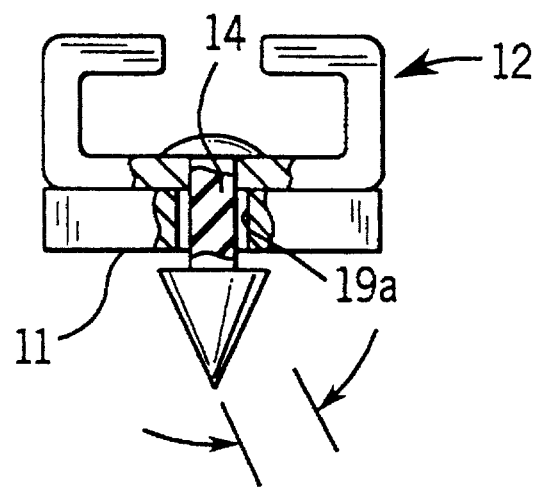
FIG. 4a is an axial section through the receiving element shown in FIGS. 1–4.

In order to increase the flexibility of the apparatus further, the receiving element 12 can be tiltable with respect to the swivel pin 14 within predetermined limits; that is, the swivel pin mounting can function to a limited extent as a universal joint. The range of tilt is substantially in the range of 5° to 25° relative to the swivel pin 14 on all sides. In order to achieve this, the swivel pin 14 can be made flexible or the receiving element 12 can be mounted on the swivel pin 14 with somewhat greater clearance than would otherwise be the case. For example, as shown in FIG. 4a which is an axial section through the unit shown in FIGS. 3 and 4, the pin 14 has a diameter less than the opening 19 and the head is spaced to all tilting in the preferred range of 5 to 25 degrees.

Figure 6:
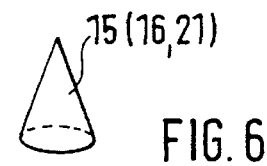
FIGS. 6 and 7 are perspective views of two spikes respectively forming part of apparatus according to the invention.
Figure 7:
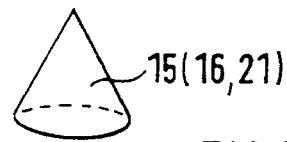

In FIGS. 6 and 7 two different types of spike or thorn 15 are illustrated. In FIG. 6 the spike 15 has the shape of a pointed cone but the spike shown in FIG. 7 is a more compressed pointed cone. The latter embodiment is characterized by the provision of a V-shaped cutting edge that facilitates penetration into the bone.

FIG. 1 shows a further bone spike or thorn 21, which is mounted on a U-shaped slide 22' so that its position along the retaining strap 10 can be adjusted. This adjustability is indicated by the double arrow 33 in FIG. 1. The slide 22' is kept on the retaining strap 10 by its two edges that are bent at successive right angles, so that they enclose the two long edges of the retaining strap 10.

Figure 8:
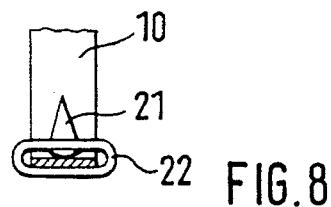
FIG. 8 is a side view of a bone spike slidable along a retaining strap, which is shown in cross-section.

Alternatively, in place of the U-shaped slide 22' shown in FIG. 1, a flat sleeve 22 slidable along the retaining strap 10 can be provided as shown in FIG. 8. The provision of a bone spike 21 that can be slid along the retaining strap 10 allows the spike 21 to be positioned according to individual requirements. In particular, loose bone fragments can be fixed in place with this slidable bone spike 21. Furthermore, suitable placement of the spike 21 can prevent slippage of the retaining strap 10 along the bone while the strap 10 is being wrapped around the bone and tightened. For this purpose, the slidable spike 21 is preferably positioned on the side of the bone opposite the site of access through a muscle incision, as illustrated in FIG. 9.

The sliding sleeve 22 and the slide 22' are preferably made from a piece of retaining strap and, in any event, from the same material as the retaining strap.

Figure 10:
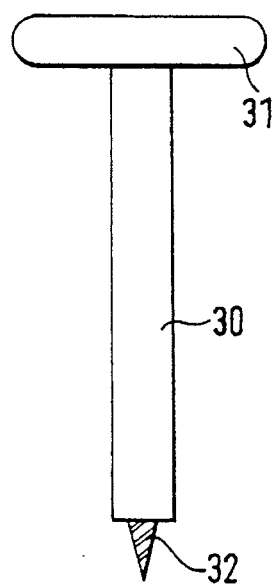
FIG. 10 is a side view of a bone drill.

At sites on the bone that are accessible through an incision, it is recommended that a hole be drilled in advance to receive a spike 15, 16 or 21. A bone-spike drill as shown in FIG. 10 can be used for this purpose; it comprises a shaft 30 at one end of which is a cross bar 31 and at the other end of which is located a pointed conical drill-bit 32. The configuration of the drill-bit 32 is similar to that of a wood drill. The cross bar 31 serves as a handle to transmit the torque for the drilling operation.

Figure 9:
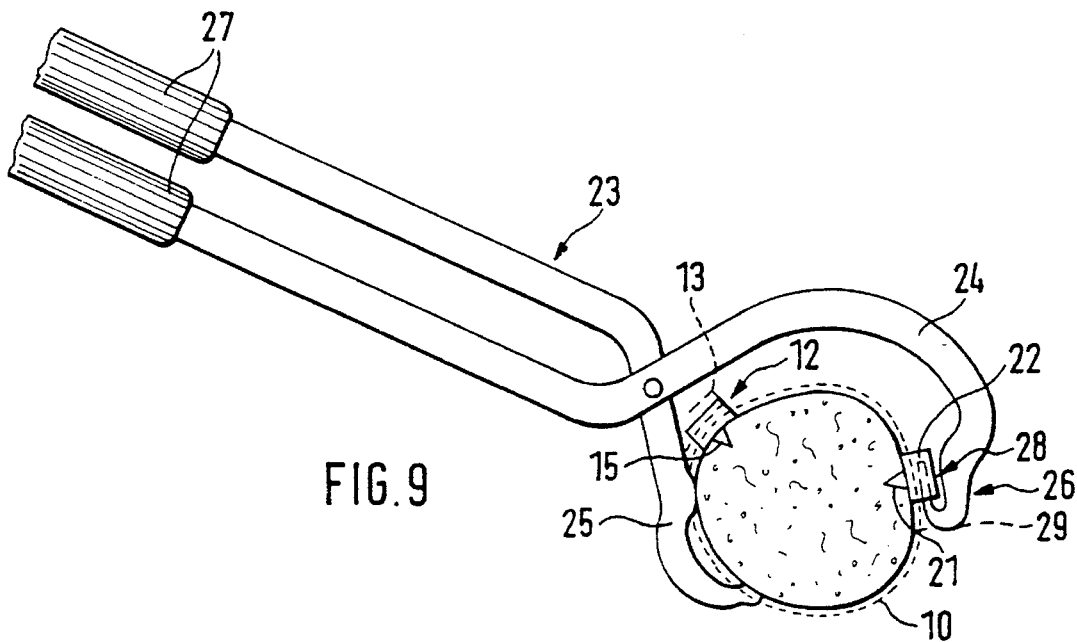
FIG. 9 is a diagram of a pair of forceps when in use to position the movable bone spike and press it into a bone.

In order to position the slidable spike 21 on the side of a bone opposite a site of access through a muscle incision, special forceps as shown diagrammatically in FIG. 9 are preferably used. This pair of forceps 23 is shaped like water-pump pliers with jaws 24 and 25, wherein one jaw 24 is substantially semicircular in shape so that its free end 26 can be passed around the bone to a position opposite the site of access. This free end 26 is provided with a holding device 28 to engage the spike 21 that is slidable along the retaining strap 10 wrapped around the bone. The holding device 28 is preferably in the form of a hooked projection 29 that extends inward, away from the free end 26 of the forceps jaw 24, so that the slidable spike 21 or its slide 22' or sliding sleeve 22 can be set onto it in such a way that when the forceps jaws 24 and 25 are pressed together via handles 27, the pressure is exerted only on the spike 21, the bone-facing side of the slide 22' or the sliding sleeve 22, and the associated section of the retaining strap 10. With this arrangement, the forceps 23 do not compress the sliding sleeve 22 or the slide 22'.

What is claimed is:

1. An apparatus for the osteosynthesis of bone fragments comprising:

a retaining strap in the form of a flat strip adapted to be wrapped around a bone in the region of a site to be treated and having a first end and second end, the first end having an axis perpendicular to the flat strip, a sleeve, a rotating connector secured to said sleeve and to said first end of said strap, said sleeve having a bore slightly larger than said second end of said strap so that said second end of the strap can be passed through said sleeve with a slight clearance, said rotating connector being secured to said sleeve in alignment with said bore and to said first end of said strap and securing said sleeve on said strap with said bore overlying said first end of said strap so that said axis passes through said rotating connector and said bore; and, a bone securing element projecting from said sleeve and strap in alignment with said sleeve to secure said first end of said strap to a bone.

2. Apparatus as claimed in claim 1, wherein said bone securing element includes at least one spike adapted to penetrate the bone with said retaining strap on the bone.

3. Apparatus as claimed in claim 1, wherein said flat strip has a rectangular cross section and the sleeve comprises a flat strap bent into a sleeve defining said bore as a substantially rectangular bore slightly larger than said cross section of the retaining strap so that said second end of the strap can be passed through the sleeve with a slight clearance.

4. Apparatus as claimed in claim 1, wherein said rotating connector includes a swivel pin secured to said sleeve and protruding therefrom and having said bone securing element in a shape of the spike for penetrating the bone with said restraining strap on the bone.

5. Apparatus as claimed in claim 1, wherein said sleeve includes radial serrations in a star pattern centered on said axis and with said serrations abutting the retaining strap.

6. Apparatus as claimed in claim 1, wherein said first end of said strap includes radial serrations in a star pattern centered on said axis and abutting the sleeve.

7. Apparatus as claimed in claim 1, wherein the bore of the sleeve includes a funnel-shaped opening having a wide end to receive said second end and tapering from said wide end to a narrow end.

8. Apparatus as claimed in claim 1, wherein said rotating structure includes a means for tilting of the sleeve relative to said strap within predefined limits.

9. Apparatus as claimed in claim 8, wherein the sleeve can be tilted in the range of 5° to 25° inclusive.

10. Apparatus as claimed in claim 8, wherein said rotating member is a flexible pin.

11. Apparatus as claimed in claim 8, wherein said rotating structure includes a swivel pin connected to the sleeve, said strap includes an opening through which said pin extends, a swivel pin with said opening of said strap having sufficient clearance to permit the sleeve to be tilted relative to said strap.

12. Apparatus as claimed in claim 1, including a movable support connected to said strap for moving along the retaining strap, and a bone spike secured to said movable support.

13. Apparatus as claimed in claim 12, wherein the movable support is a slidable sleeve.

14. Apparatus as claimed in claim 13, wherein the slidable sleeve comprises a substantially U-shaped slide that can be moved along the retaining strap.

* * * * *